United States Patent

Outtrup et al.

Patent Number: 5,531,918
Date of Patent: Jul. 2, 1996

[54] NOVEL PROTEASES

[75] Inventors: Helle Outtrup, Ballerup; Claus Dambmann, Soeborg; Dorrit A. Aaslyng, Roskilde; Poul Lindegaard, Copenhagen, all of Denmark

[73] Assignee: Novo Nordisk A/S, Bagsvaerd, Denmark

[21] Appl. No.: 290,932

[22] PCT Filed: Mar. 3, 1993

[86] PCT No.: PCT/DK93/00074

§ 371 Date: Aug. 22, 1994

§ 102(e) Date: Aug. 22, 1994

[87] PCT Pub. No.: WO93/18140

PCT Pub. Date: Sep. 16, 1993

[30] Foreign Application Priority Data

Mar. 4, 1992 [DK] Denmark ..................... 287/92

[51] Int. Cl.$^6$ ................................. C11D 3/386
[52] U.S. Cl. ................ 510/320; 435/221; 510/321; 510/392; 510/393; 510/530
[58] Field of Search ............... 252/176.12, DIG. 12; 435/219, 220, 221

[56] References Cited

U.S. PATENT DOCUMENTS

| | | | |
|---|---|---|---|
| 4,480,037 | 10/1984 | Ichisima et al. | 435/221 |
| 4,764,470 | 8/1988 | Durham et al. | 435/221 |
| 4,771,003 | 9/1988 | Stellwag et al. | 435/221 |
| 5,387,518 | 2/1995 | Sawayanagi et al. | 435/221 |

FOREIGN PATENT DOCUMENTS

| | | |
|---|---|---|
| 0495405A1 | 1/1992 | European Pat. Off. . |
| 0495401 | 9/1992 | European Pat. Off. .......... C12N 9/54 |

*Primary Examiner*—Glenn Caldarola
*Assistant Examiner*—Alexander G. Ghyka
*Attorney, Agent, or Firm*—Steve T. Zelson; Elias J. Lambiris

[57] ABSTRACT

The present invention relates to proteases obtained from a strain of *Bacillus sp.* PD138, detergent additives and compositions comprising a *Bacillus sp.* PD138 protease, and methods of making and using a *Bacillus sp.* PD138 protease.

8 Claims, 1 Drawing Sheet

NOVEL PROTEASES

CROSS-REFERENCE TO RELATED APPLICATIONS

This application is a continuation of PCT/DK93/00074 filed Mar. 3, 1993, the contents of which are incorporated herein by reference.

TECHNICAL FIELD

This invention is in the field of detergent proteases derived from strains of *Bacillus sp*. More specifically, the invention is directed towards a novel alkaline protease derived from a strain of *Bacillus sp*. PD138. Moreover, the invention is directed towards a process for the preparation of the protease, the use of the protease as detergent enzyme, and detergent compositions comprising the protease of the invention.

BACKGROUND ART

Detergent enzymes have been marketed for more than 20 years and are now well established as normal detergent ingredients in both powder and liquid detergents all over the world. With the trend towards lower temperature washing, detergent enzyme consumption has increased during late years. Enzymes used in washing formulations comprise proteases, lipases, amylases, cellulases, as well as other enzymes, or mixtures hereof. Commercially most important are proteases.

Detergent proteases have been developed by isolation of proteases found in nature followed by testing in detergent formulations. Most detergent proteases are obtained from members of the genus Bacillus. Currently new types of proteases enter the market, offering the possibility of giving a better cost/performance ratio at various specified conditions.

Examples of commercial protease products are ALCALASE™, ESPERASE™ and SAVINASE™, all supplied by Novo Nordisk A/S, Denmark. These and similar enzyme products from other commercial sources are active in detergent solutions, i.e. at pH values in the range of from 8 to 11 and in the presence of sequestering agents, surfactants and bleaching agents such as sodium borate. The ALCALASE™ protease is produced by strains of the species *Bacillus licheniformis*. The ESPERASE™ and SAVINASE™ proteases are obtained by cultivation of strains of alkalophilic Bacilli.

SUMMARY OF THE INVENTION

It is an object of the present invention to provide novel detergent proteases with improved washing performance at high pH and high ion strength.

Accordingly, in its first aspect, the invention provides a protease having an apparent molecular weight of 28 kD, pI above 9.5, pH optimum at pH 11 or above (at 25° C.), temperature optimum in the range of from 45° to 55° C. (at pH 9.5), and immunochemical properties identical or partially identical to those of a protease derived from the strain *Bacillus sp*. PD138, NCIMB 40338.

In a second aspect, the invention relates to an isolated biologically pure culture of a strain of *Bacillus sp*. represented by the strain *Bacillus sp*. PD138. In a more specific aspect, the invention relates to a strain of *Bacillus sp*. PD138, NCIMB 40338, or a mutant or a variant thereof.

In a third aspect, the invention provides a process for the preparation of the protease, which process comprises cultivation of a protease producing strain of *Bacillus sp*. PD138 in a suitable nutrient medium, containing carbon and nitrogen sources and inorganic salts, followed by recovery of the desired enzyme. In a more specific aspect, *Bacillus sp*. PD138, NCIMB 40338, or a mutant or a variant thereof, or another host organism carrying the gene encoding a protease having immunochemical properties identical or partially identical to those of the protease derived from *Bacillus sp*. PD138, is cultivated.

In a fourth aspect, the use of the enzyme as detergent enzyme is claimed. In more specific aspects, the invention provides detergent compositions and detergent additives comprising the protease.

In a fifth aspect, the invention provides a washing process comprising addition of the protease.

BRIEF DESCRIPTION OF DRAWINGS

The present invention is further illustrated by reference to the accompanying drawings, in which.

DETAILED DISCLOSURE OF THE INVENTION

The Microorganism

Figure 1:
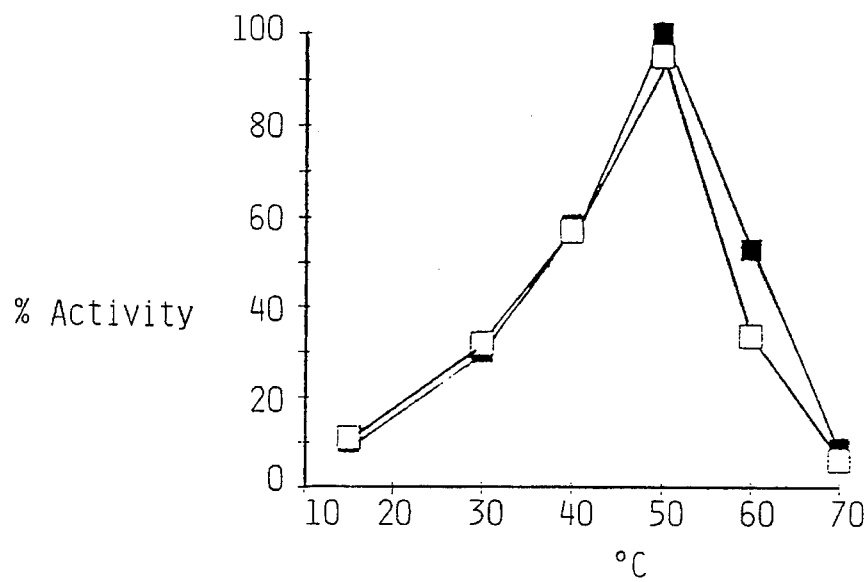
FIG. 1 shows the relation between temperature and the proteolytic activity of an enzyme according to the invention (the enzyme preparation obtained according to Ex. 1, with 2% of casein as substrate and at pH 9.5; ■ Buffer, □ Buffer +0.1% of STPP).

The novel microorganism of the invention, able to produce an enzyme of the invention, is represented by the strain that was isolated from a sample of Jamaican soil. *Bacillus sp*. PD138, has been deposited according to the Budapest Treaty on the International Recognition of the Deposits of Microorganisms for the Purpose of Patent Procedures, on 3 Dec. 1990 at National Collections of Industrial and Marine Bacteria Ltd. (NCIMB), 23 St. Machar Drive, Aberdeen AB2 1RY, Scotland, UK, under Accession No. NCIMB 40338.

The microorganism of this invention is an aerobic, spore forming bacterium belonging to the genus Bacillus. Morphologically it can be described as motile rods with a diameter of 0.7–0.9 micron, and a length of 2–3 micron. The spores are round to ellipsoid, not swelling the sporangium, central to subterminal. Optimum temperature for growth is within 25°–37° C., and optimal pH for growth is within 7–9, no growth at pH 9.7, and no growth at 50° C. The microorganism forms yellowish to yellow colonies, round and smooth, on nutrient agar slants, and no diffusion of pigment into the agar is observed.

Cultivation of the Microorganism

The microorganism of the invention can be cultivated under aerobic conditions in a nutrient medium containing assimilable carbon and nitrogen together with other essential nutrients, the medium being composed in accordance with the principles of the known art, Suitable carbon sources are carbohydrates such as sucrose, glucose and starch, or carbohydrate containing materials such as cereal grain, malt, rice and sorghum. The carbohydrate concentration incorporated in the medium may vary widely, e.g. up to 25% and down to 1–5%, but usually 8–10% will be suitable, the percentages being calculated as equivalents of glucose.

The nitrogen source in the nutrient medium may be of inorganic and/or organic nature. Suitable inorganic nitrogen sources are nitrates and ammonium salts. Among the organic nitrogen sources quite a number are used regularly in fermentation processes involving the cultivation of bacteria. Illustrative examples are soybean meal, cotton seed meal, peanut meal, casein, corn, corn steep liquor, yeast extract, urea, and albumin. In addition, the nutrient medium should also contain usual trace substances.

The novel *Bacillus species* of this invention are slightly alkalophilic. Therefore, the cultivation is preferably conducted at slightly alkaline pH values, which is can be obtained by addition of suitable buffers such as sodium bicarbonate, pH 9.0, after sterilization of the growth medium. For cultivation in tank fermentors it is necessary to use artificial aeration. The rate of aeration is similar to that used in conventional tank fermentation.

After fermentation, liquid enzyme; concentrates may be produced by removal of coarse material from the broth or, if desired, concentration of the broth by evaporation at low temperature or by reverse osmosis. Finally, preservatives may be added to the concentrate.

Solid enzyme preparations may be prepared from the purified and/or concentrated broth by precipitation with salts, such as $Na_2SO_4$ or water-miscible solvents, such as ethanol or acetone. Removal of the water in the broth by suitable drying methods, such as spray-drying, may also be employed.

Assay for Proteolytic Activity

The proteolytic activity is determined with casein as substrate. One Casein Protease Unit (CPU) is defined as the amount of enzyme liberating 1 mM of primary amino groups (determined by comparison with a serine standard) per minute under standard conditions, i.e. incubation for 30 minutes at 25° C. and pH 9.5. A folder AF 228, describing the analytical method, is available upon request to Novo Nordisk A/S, Denmark, which folder is hereby included by reference.

The Enzyme

The enzyme of the invention is a novel detergent protease. It is an alkaline protease, obtainable by cultivation of a microorganism of the invention, preferably Bacillus sp. PD138, NCIMB 40338, or a mutant or a variant thereof, in a suitable nutrient medium, containing carbon and nitrogen sources and inorganic salts. The enzyme can also be obtained by recombinant DNA-technology.

The protease of the invention can be described by the following characteristics.

Physical-Chemical Properties

A molecular weight of 28 kD, determined by SDS-PAGE. A pI above 9.5 could not be accurately determined by isoelectric focusing on LKB Ampholine® PAG plates. The protease activity is inhibited by PMSF, α-1-antitrypsin, and Turkey-egg-white proteinase inhibitor. EDTA and soybean-protein inhibitor do not influence the protease activity.

The temperature activity relationship was determined with 2% of casein as substrate and at pH 9.5 in the presence (white squares) and absence (black squares) of 0.1% of sodium tripolyphosphate (STPP, a common ingredient in many commercial detergents). The assay for proteolytic activity described previously was used with the modification that the incubation temperature was varied in the interval of from 15° to 70° C.

The result is shown in FIG. 1: It appears from the figure that the enzyme possesses proteolytic activity from temperatures below 15° C. to above 70° C., and has a temperature optimum within the range of 45° to 55° C., around 50° C.

The dependence of activity on pH was determined by the same procedure using buffers adjusted to predetermined pH values in the pH range of from 6 to 11.

Figure 2:
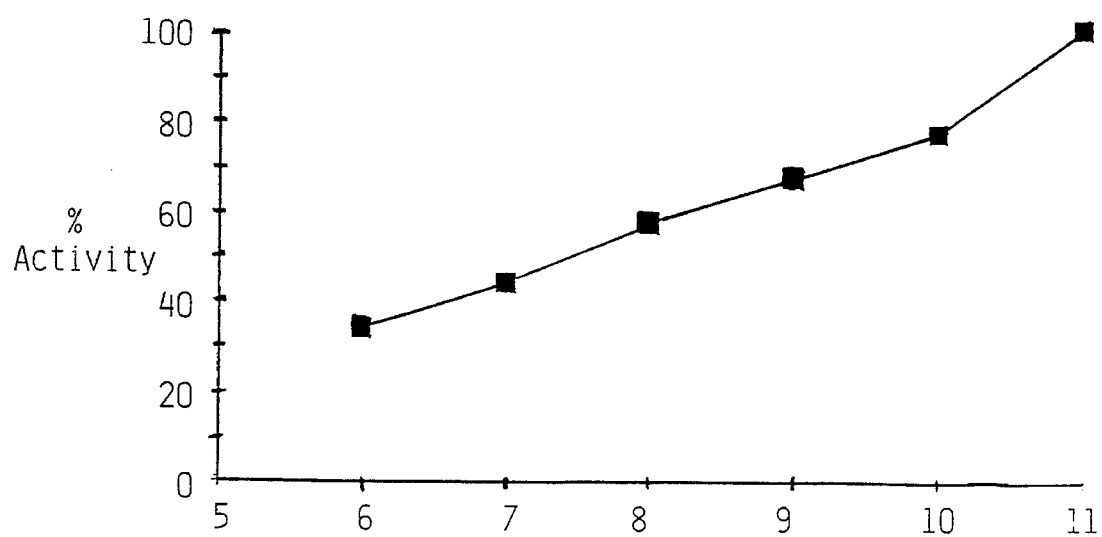
FIG. 2 shows the relation between pH and the proteolytic activity of an enzyme according to the invention (the enzyme preparation obtained according to. Ex. 1, with 1% of casein as substrate and at 25° C.).

The result is shown in FIG. 2. It appears from this figure that the enzyme possesses proteolytic activity at pH values below 6 to above 11, with a pH optimum above pH 10, more specifically with a pH optimum of at least pH 11.

Furthermore, it was found that the protease of the invention is stable for 60 minutes at 25° C. under washing conditions, in European type and American type detergents.

The protease of the invention possesses especial potentials in detergents with high ionic strength and high pH. From the wash performance test, cf. Ex. 2, during wash at pH 11 in 9° dH (German Hardness) water, a washing performance far superior to that of the alkaline Bacillus protease SAVINASE™ (Novo Nordisk A/S, Denmark) appeared.

Immunochemical Properties

The protease of the invention has immunochemical properties identical or partially identical (i.e. at least partially identical) to those of a protease derived from the strain *Bacillus sp.* PD138, NCIMB 40338.

The immunochemical properties can be determinated immunologically by cross-reaction identity tests. The identity tests can be performed by the well-known Ouchterlony double immunodiffusion procedure or by tandem crossed immunoelectrophoresis according to N. H. Axelsen; Handbook of Immunoprecipitation-in-Gel Techniques; Blackwell Scientific Publications (1983), chapters 5 and 14. The terms "antigenic identity" and "partial antigenic identity" are described in the same book, chapters 5, 19 and 20.

Monospecific antiserum was generated according to the above mentioned method by immunizing rabbits with the purified protease of the invention. The immunogen was mixed with Freund's adjuvant and injected subcutaneously into rabbits every second week. Antiserum was obtained after a total immunization period of 8 weeks, and immunoglobulin was prepared therefrom as described by N. H. Axelsen, supra.

Ouchterlony double immunodiffusion tests showed no cross reaction between the protease of the invention and the known alkaline serine proteases ALCALASE™, SAVINASE™, ESPERASE™, subtilisin Novo (available from Novo Nordisk A/S), and KAZUSASE™ (available from SHOWA DENKO).

Detergent Compositions

According to the the invention, the protease may typically be added as a component of a detergent composition. As such, it may be included in the detergent composition in the form of a detergent additive. The detergent composition as well as the detergent additive may additionally comprise one or more other enzymes conventionally used in detergents, such as lipases, amylases, cellulases, oxidases or peroxidases.

In a specific aspect, the invention provides a detergent additive. The enzymes may be included in a detergent composition by adding separate additives containing one or more enzymes, or by adding a combined additive comprising all of these enzymes.

Preferably, the detergent additive, i.e. a separated additive or a combined additive, is provided in the form of a granulate, preferably a non-dusting granulate, a liquid, in particular a stabilized liquid, a slurry, or in a protected form.

Dust free granulates may be produced, e.g. as disclosed in U.S. Pat. No. 4,106,991 and U.S. Pat. No. 4,661,452 (both to Novo Industri A/S) and may optionally be coated by methods known in the art. The detergent enzymes may be mixed before or after granulation.

Liquid enzyme preparations may, for instance, be stabilized by adding a polyol such as propylene glycol, a sugar or sugar alcohol, lactic acid or boric acid, according to established methods. Other enzyme stabilizers are well known in the art.

Protected enzymes may be prepared according to the method disclosed in EP 238,216 A.

The detergent composition of the invention may be in any convenient form, e.g. as powder, granules or liquid. A liquid detergent may be aqueous, typically containing up to 90% of water and 0–20% of organic solvent.

The detergent composition comprises a surfactant which may be anionic, non-ionic, cationic, amphoteric or a mixture of these types. The detergent will usually contain 0–50% of anionic surfactant such as linear alkyl benzene sulphonate (LAS), alpha-olefin sulphonate (AOS), alkyl sulphate (AS), alcohol ethoxy sulphate (AES) or soap. It may also contain 0–40% of non-ionic surfactant such as nonyl phenol ethoxylate or alcohol ethoxylate. Furthermore, it may contain a polyhydroxy fatty acid amide surfactant (e.g. as described in WO 92/06154).

The pH (measured in aqueous detergent solution) will usually be neutral or alkaline, e.g. 7–11. The detergent may contain 1–40% of a detergent builder such as zeolite, phosphate, phosphonate, citrate, NTA, EDTA or DTPA, alkenyl succinic anhydride, or silicate, or it may be unbuilt (i.e. essentially free of a detergent builder). It may also contain other conventional detergent ingredients, e.g. fabric conditioners, foam boosters, bleaching agents, e.g. perborate, percarbonate, tetraacetyl ethylene diamine (TAED), or nonanoyloxybenzene sulfonate (NOBS), anticorrosion agents, soil-suspending agents, sequestering agents, anti-soil redeposition agents, stabilizing agents for the enzyme(s), foam depressors, dyes, bactericides, optical brighteners or perfumes.

Particular forms of detergent composition within the scope of the invention include:

a) A detergent composition formulated as a detergent powder containing phosphate builder, anionic surfactant, nonionic surfactant, silicate, alkali to adjust to desired pH in use, and neutral inorganic salt.

b) A detergent composition formulated as a detergent powder containing zeolite builder, anionic surfactant, nonionic surfactant, acrylic or equivalent polymer, silicate, alkali to adjust to desired pH in use, and neutral inorganic salt.

c) A detergent composition formulated as an aqueous detergent liquid comprising anionic surfactant, nonionic surfactant, humectant, organic acid, caustic alkali, with a pH in use adjusted to a value between 7 and 10.5.

d) A detergent composition formulated as a nonaqueous detergent liquid comprising a liquid nonionic surfactant consisting essentially of linear alkoxylated primary alcohol, phosphate builder, caustic alkali, with a pH in use adjusted to a value between about 7 and 10.5.

e) A detergent composition formulated as a detergent powder in the form of a granulate having a bulk density of at least 600 g/l, containing anionic surfactant and nonionic surfactant, low or substantially zero neutral inorganic salt, phosphate builder, and sodium silicate.

f) A detergent composition formulated as a detergent powder in the form of a granulate having a bulk density of at least 600 g/l, containing anionic surfactant and nonionic surfactant, low or substantially zero neutral inorganic salt, zeolite builder, and sodium silicate.

g) A detergent composition formulated as a detergent powder containing anionic surfactant, nonionic surfactant, acrylic polymer, fatty acid soap, sodium carbonate, sodium sulphate, clay particles, and sodium silicate.

h) A liquid compact detergent comprising 5–65% by weight of surfactant, 0–50% by weight of builder and 0–30% by weight of electrolyte.

It is at present contemplated that, in the detergent composition of the invention, the [?protease] may be added in an amount corresponding to [?0.001–100] mg of enzyme per liter of wash liquor.

The invention is further illustrated in the following examples, which are not intended to be in any way limiting to the scope of the invention as claimed.

EXAMPLE 1

*Bacillus sp.* PD138, NCIMB 40338, was cultivated at 25° C. on a rotary shaking table (300 r.p.m.) in 500 ml baffled Erlenmeyer flasks containing 100 ml of medium of the following composition (per liter):

| | |
|---|---|
| Potato starch | 100 g |
| Ground barley | 50 g |
| Soybean flour | 20 g |
| $Na_2HPO_4 \times 12H_2O$ | 9 g |
| Pluronic ® | 0.1 g |
| Sodium caseinate | 10 g |

The starch in the medium is liquified with α-amylase, and the medium is sterilized by heating at 120° C. for 45 minutes.

After sterilization the pH of the medium is adjusted to 9.0 by addition of 10 ml of a 1 M solution of sodium bicarbonate.

After 4 days of incubation the proteolytic activity of the culture was determined using the method described above.

After cultivation, the enzyme activity of the broth was 20 CPU/l.

After separation of the solid material the protease was purificated by a conventional chromatographic method.

Yield from 1 l of culture broth was 50 ml with 100 CPU/l. Purity was more than 90% as judged by SDS-PAGE.

The characteristics of the preparation prepared in accordance with this Example have been referred to earlier in this specification, and reference is made hereto.

EXAMPLE 2

Wash Performance

The wash performance tests were accomplished on grass soiled cotton, at 40° C., isothermally for 10 minutes.

The tests were performed at enzyme concentrations of 0.01, 0.025, 0.05, 0.1, 0.5, and 1.0 mg of enzyme protein per liter.

5.0 g/l of a commercial European compact powder detergent were used. The detergent was dissolved in approx. 9° dH (German Hardness) water, and pH was adjusted to 11.

The textile/wash liquor ratio was 6 g of textile per liter of wash liquor.

Subsequent to washing, the cloths were flushed in running tap water and air-dried. The remission (%R) at 460 nm was determined.

As a measure of the wash performance differential remission, ΔR, was used being equal to the remission after wash with enzyme added, minus the remission after wash with no enzyme added.

The results of these tests are shown in Table 1 below (mean of 2 tests).

TABLE 1

| Enzyme Concentration | delta R | |
|---|---|---|
| (mg enzyme protein/liter) | PD138 | SAVINASE ™ |
| 0.01 | 5.7 | 3.2 |
| 0.025 | 13.5 | — |
| 0.05 | 19.4 | 8.1 |
| 0.10 | 22.0 | 14.8 |
| 0.50 | 22.6 | 22.0 |
| 1.0 | — | 22.2 |

(— not done)

The differential remission values show that the protease of the invention has especial potentials in detergents with high ionic strength and high pH, where it possesses good washability.

We claim:

1. A protease obtained from a strain of *Bacillus sp.* PD138 having the following properties:

(a) an apparent molecular weight of 28 kD;

(b) an isoelectric point above 9.5;

(c) a pH optimum above 10 at 25° C. and with casein as substrate; and (d) a temperature optimum in the range of from 45° to 55° C. at pH 9.5 and with casein as substrate.

2. The protease according to claim 1, wherein the strain is NCIMB 40338 or a mutant thereof.

3. A process for producing a protease according to claim 1, comprises (a) cultivating a strain of *Bacillus sp.* in a suitable nutrient medium containing carbon and nitrogen sources and inorganic salts; and (b) recovering the protease.

4. The process according to claim 3, wherein the strain is *Bacillus sp.* PD138, NCIMB 40338, or a mutant thereof.

5. A detergent composition comprising a surfactant and a protease according to claim 1.

6. The detergent composition according to claim 5, further comprising one or more other enzymes selected from the group consisting of an amylase, a lipase, a cellulase, a peroxidase, and an oxidase.

7. A detergent additive comprising a protease according to claim 1 in the form selected from the group consisting of a non-dusting granulate, a liquid, a slurry, and a protected enzyme.

8. A method for washing a fabric, comprising adding to the fabric a protease according to claim 1.

* * * * *